United States Patent
Yachia et al.

(10) Patent No.: US 10,327,883 B2
(45) Date of Patent: Jun. 25, 2019

(54) FILTRATION AND ENTRAPMENT APPARATUS AND METHOD OF USE

(71) Applicant: INNOVENTIONS LTD., Or Akiva (IL)

(72) Inventors: Daniel Yachia, Herzlia (IL); Valentin Ponomarenko, Haifa (IL)

(73) Assignee: Innovations LTD., Or Akiva (IL)

( * ) Notice: Subject to any disclaimer, the term of this patent is extended or adjusted under 35 U.S.C. 154(b) by 203 days.

(21) Appl. No.: 15/100,309

(22) PCT Filed: Nov. 27, 2014

(86) PCT No.: PCT/IB2014/066389
§ 371 (c)(1),
(2) Date: May 29, 2016

(87) PCT Pub. No.: WO2015/079401
PCT Pub. Date: Jun. 4, 2015

(65) Prior Publication Data
US 2016/0296315 A1  Oct. 13, 2016

Related U.S. Application Data

(60) Provisional application No. 61/910,065, filed on Nov. 28, 2013.

(51) Int. Cl.
*A61F 2/01* (2006.01)
*A61F 2/24* (2006.01)

(52) U.S. Cl.
CPC ............ *A61F 2/013* (2013.01); *A61F 2/2427* (2013.01); *A61F 2002/011* (2013.01); *A61F 2002/016* (2013.01); *A61F 2230/0067* (2013.01); *A61F 2230/0091* (2013.01)

(58) Field of Classification Search
CPC .. A61F 2/013; A61F 2/2427; A61F 2002/016; A61F 2230/0091; A61F 2002/011; A61F 2230/0067
See application file for complete search history.

(56) References Cited

U.S. PATENT DOCUMENTS

| 5,662,671 | A | * | 9/1997 | Barbut | A61B 17/32078 604/104 |
| 5,690,644 | A | * | 11/1997 | Yurek | A61F 2/95 606/198 |
| 7,367,985 | B2 | * | 5/2008 | Mazzocchi | A61B 17/12022 606/108 |
| 7,367,986 | B2 | * | 5/2008 | Mazzocchi | A61B 17/12022 606/108 |
| 7,371,250 | B2 | * | 5/2008 | Mazzocchi | A61B 17/12022 606/108 |

(Continued)

*Primary Examiner* — Phong Son H Dang
(74) *Attorney, Agent, or Firm* — Robert G. Lev

(57) ABSTRACT

A filter system comprises an expandable filter, with a first end of the filter attached to an end of a first tube, and a second end of the filter attached to an end of a second tube. The tubes are arranged telescopically with respect to each other such that telescopic movement of the first and second tubes with respect to each other causes the filter to move between a first collapsed, position and a second expanded position, where the filter extends outwardly. The filter may be a folded-over member, when in the expanded position, or a spiraling member.

22 Claims, 11 Drawing Sheets

(56) References Cited

U.S. PATENT DOCUMENTS

| | | | | |
|---|---|---|---|---|
| 7,815,676 B2* | 10/2010 | Greenberg | A61B 17/22 | 623/2.11 |
| 8,016,872 B2* | 9/2011 | Parker | A61F 2/95 | 623/1.11 |
| 8,252,017 B2* | 8/2012 | Paul, Jr. | A61F 2/013 | 606/200 |
| 8,721,714 B2* | 5/2014 | Kelley | A61F 2/2436 | 623/2.11 |
| 8,795,305 B2* | 8/2014 | Martin | A61F 2/06 | 606/159 |
| 9,138,307 B2* | 9/2015 | Valaie | A61B 17/320725 | |
| 9,907,639 B2* | 3/2018 | DeBruyne | A61F 2/07 | |
| 2002/0072765 A1* | 6/2002 | Mazzocchi | A61B 17/12022 | 606/200 |
| 2002/0138095 A1* | 9/2002 | Mazzocchi | A61B 17/12022 | 606/200 |
| 2002/0169474 A1* | 11/2002 | Kusleika | A61F 2/013 | 606/200 |
| 2003/0176884 A1* | 9/2003 | Berrada | A61F 2/013 | 606/200 |
| 2006/0025844 A1* | 2/2006 | Majercak | A61F 2/95 | 623/1.11 |
| 2006/0030923 A1* | 2/2006 | Gunderson | A61F 2/95 | 623/1.11 |
| 2006/0041302 A1* | 2/2006 | Malewicz | A61F 2/95 | 623/1.11 |
| 2006/0200221 A1* | 9/2006 | Malewicz | A61F 2/966 | 623/1.11 |
| 2007/0112374 A1* | 5/2007 | Paul, Jr. | A61F 2/013 | 606/200 |
| 2007/0149996 A1* | 6/2007 | Coughlin | A61F 2/013 | 606/200 |
| 2014/0276403 A1* | 9/2014 | Follmer | A61B 17/22032 | 604/103.02 |
| 2017/0259042 A1* | 9/2017 | Nguyen | A61B 17/22032 | |

\* cited by examiner

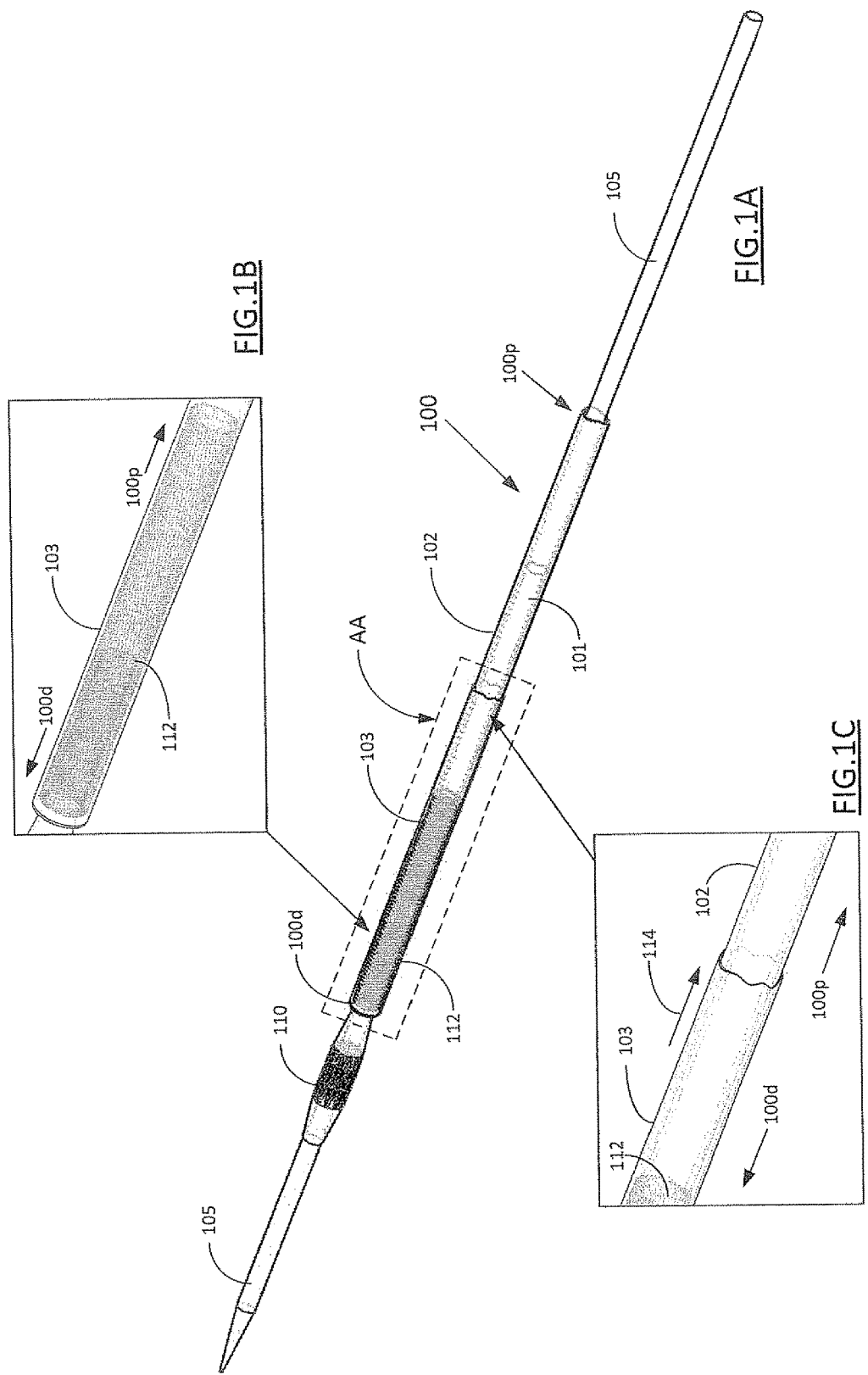

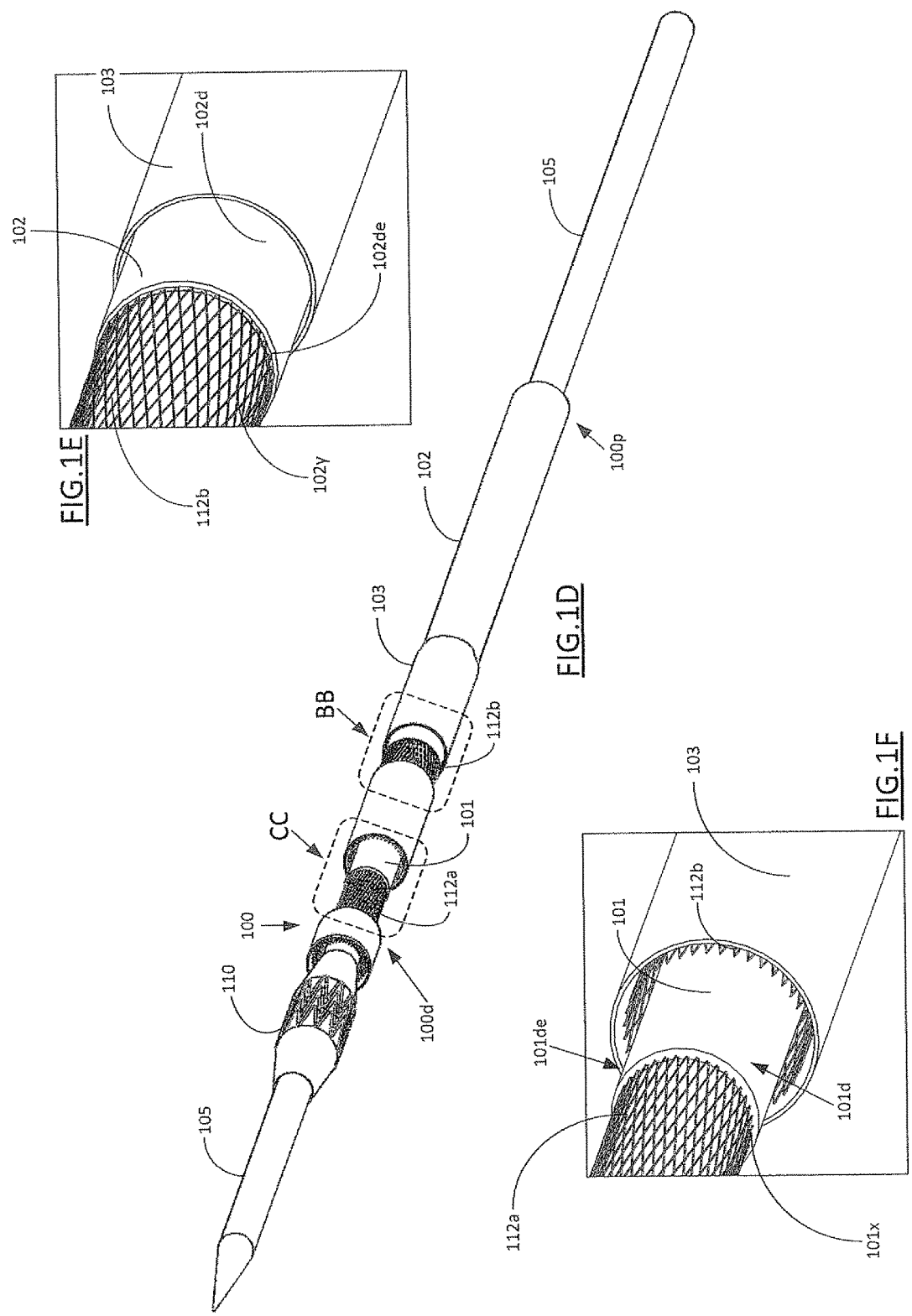

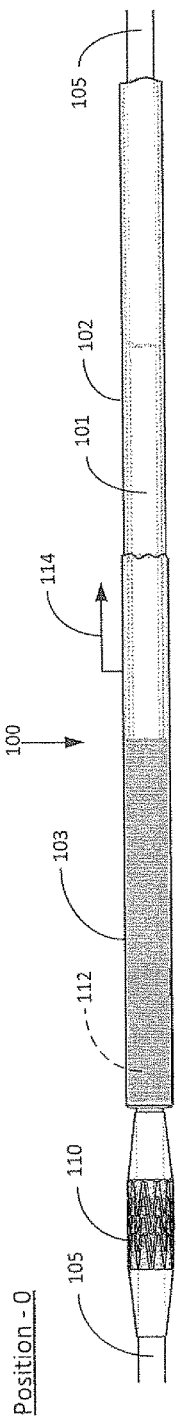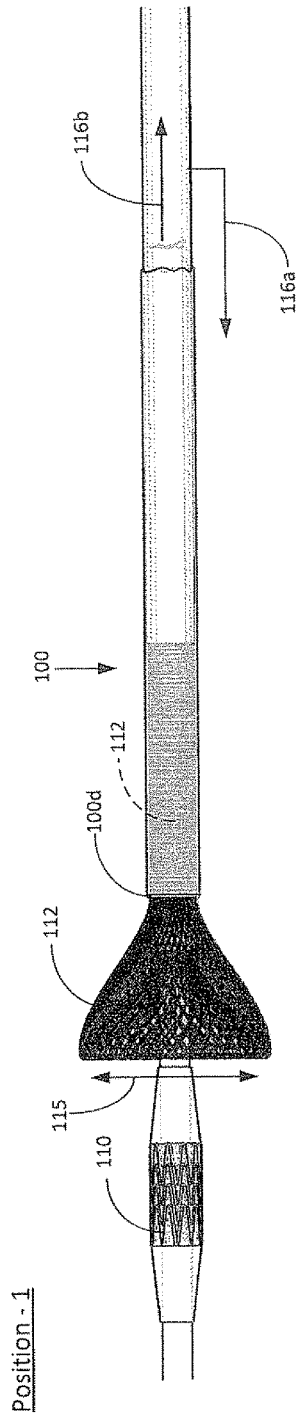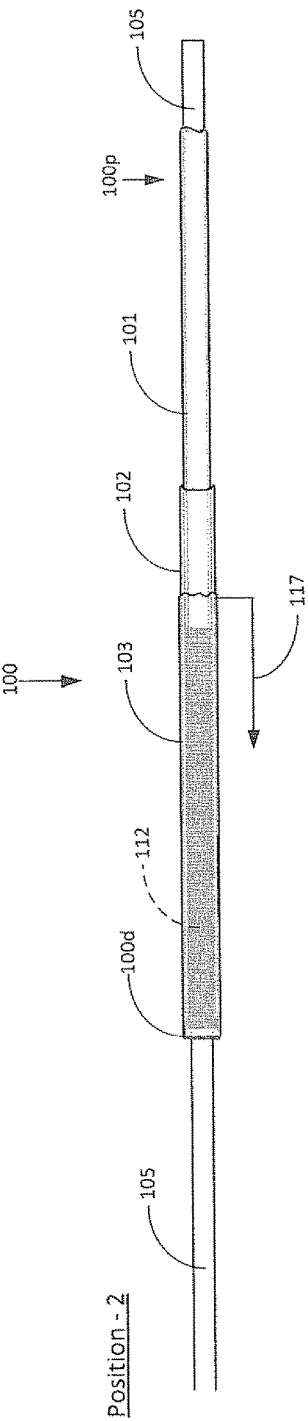

FILTRATION AND ENTRAPMENT APPARATUS AND METHOD OF USE

CROSS REFERENCES TO RELATED APPLICATIONS

This patent application is related to and claims priority from commonly owned U.S. Provisional Patent Application Ser. No. 61/910,065, entitled: FILTRATION AND ENTRAPMENT APPARATUS AND METHOD OF USE, filed on Nov. 28, 2013, the disclosure of which is incorporated by reference herein in its entirety.

BACKGROUND

The present invention relates to filtration devices for use in surgical settings inside the body. During surgical procedures, such as cardiovascular procedures, for example, valve replacement, there is a possibility that particulate and tissue matter can break away from the main tissue and enter the blood stream. If this particulate enters the blood stream, it can clog blood vessels, for example, in the brain, leading to a stroke, or in the lungs, kidneys or intestines leading to an embolism, all catastrophic conditions. It is believed that these situations may occur in up to 15% of cardiovascular surgeries and procedures.

Current technology uses filters, to cover the connection points of the vessels reaching the brain in the aortic arch, but does not filter any particulates that may flow through the aortic arch into the blood stream of the descending aorta. Accordingly, the potential for some of the catastrophic dangers remain.

SUMMARY

Embodiments of the present invention are directed to filter systems which comprise an expandable filter, with a first end of the filter attached to an end of a first tube, and a second end of the filter attached to an end of a second tube. The tubes are arranged telescopically with respect to each other such that telescopic movement of the first and second tubes with respect to each other causes the filter to move between a first collapsed position and a second expanded position, where the filter extends outwardly. The filter may be a folded-over member, when in the expanded position, or a spiraling member.

Embodiments of the present invention are directed to filters, that are introduced to surgical sites in a collapsed position, and are then expand to an outwardly expanded or extended position upon being released at the surgical site by the movement or withdrawing of a covering tube, or overtube. The filters, along the edges, appose to the vessel wall, with the requite vessel of tissue, preventing particulates from a surgical site from moving beyond the surgical site and into the circulation, or tissue, where such particulates could cause catastrophic damage. The filters are typically multi-layered, in order to maximize the amount of particulates which can be captured and trapped.

Embodiments of the present invention are directed to a filter system. The filter system comprises: a first tube; a second tube, the first tube and second tube movable relative to each other in at least a partially telescoping arrangement; and, a filter. The filter is such that s first end of the filter is supported by the first tube and a second end of the filter is supported by the second tube, and the filter is movable between a collapsed position, when at least partially covered by the second tube, and an expanded position, when uncovered by the second tube.

Optionally, the filter comprises a foldable member movable by the movement of the first and second tubes from a folded-over outwardly expanded orientation, defining the expanded position, to an inverted orientation defining the collapsed position.

Optionally, the filter system additionally comprises: a third over tube for enveloping the first and second tubes, the first tube defining an inner tube and the second tube defining a mid tube, the third tube moveable so as to cover and uncover the filter, the first, second and third tubes moveable with respect to each other.

Optionally, the first, second, and third tubes are telescopically arranged with respect to each other.

Optionally, the filter includes a frame and a mesh covering the frame.

Optionally, each of the first, second, and third tubes include a longitudinally extending slit for allowing the first, second and third tube to temporarily separate laterally outward along the longitudinally extending slit to accommodate instrumentation passing through the first, second and third tubes.

Optionally, the first second and third tubes are made of a resilient material to accommodate laterally outward movement of the tube portions on oppositely disposed sides of the longitudinally extending slit from an open closed position to an open position and the for returning the first, second, and third tubes to the closed position once the instrumentation has passed through the first, second, and third, tubes.

Optionally, the filter system additionally comprises: a delivery catheter for passage of instrumentation through the inner tube to a predetermined site and the instrumentation includes at least one of stents and valves.

Optionally, the filter comprises: a wire including a first end in communication with the first tube, and, a second end extending into the second tube; and, a net supported by the wire, to define a filter.

Optionally, the wire defines the periphery of the filter.

Optionally, the net extends from the first tube to the wire and the net runs along the first tube.

Optionally, the wire is of a resilient material and exhibits spring-like behavior.

Optionally, the wire extends along the first tube in a helical orientation between the first end of the wire and the second end of the wire.

Optionally, the wire extends through the second tube to outside the filter system.

Optionally, the wire attaches to the second tube.

Optionally, the filter system additionally comprises a third tube for moving over at least a portion of the first tube and at least a portion of the second tube, the third tube for enveloping the filter in the collapsed position, and for moving beyond the filter when the filter is in the expanded position.

Embodiments of the present invention are directed to a filter system. The filter system comprises: an outwardly expandable filter, with a first end of the filter attached to an end of a first tube, and a second end of the filter attached to an end of a second tube. The first and second tubes arranged telescopically with respect to each other such that telescopic movement of the first and second tubes with respect to each other causes the filter to move from a folded-over outwardly expanded orientation to an inverted orientation.

Optionally, the filter system additionally comprises: a third over tube for enveloping the first and second tubes, the first tube defining an inner tube and the second tube defining a mid tube, the third tube moveable so as to cover and uncover the filter, the first, second and third tubes moveable with respect to each other.

Optionally, the first, second, and third tubes are telescopically arranged with respect to each other.

Optionally, the filter includes a frame and a mesh covering the frame.

Optionally, each of the first, second, and third tubes include a longitudinally extending slit for allowing the first, second and third tube to temporarily separate laterally outward along the longitudinally extending slit to accommodate instrumentation passing through the first, second and third tubes.

Optionally, the first second and third tubes are made of a resilient material to accommodate laterally outward movement of the tube portions on oppositely disposed sides of the longitudinally extending slit from an open closed position to an open position and the for returning the first, second, and third tubes to the closed position once the instrumentation has passed through the first, second, and third, tubes.

Optionally, the filter system additionally comprises: a delivery catheter for passage of instrumentation through the inner tube to a predetermined site.

Optionally, the instrumentation includes at least one of stents and valves.

Optionally, the filter system additionally comprises: a delivery catheter for passage of the instrumentation through the inner tube to a predetermined site, and optionally, the instrumentation includes at least one of stents and valves.

Embodiments of the present invention are also directed to another filter system. The filter system comprises: a first tube and a second tube, with the first tube moveable at least partially within the second tube; and, a filter moveable between a collapsed position and an expanded position. The filter includes, a wire including a first end in communication with the first tube, and, a second end extending into the second tube; and, a net supported by the wire, to define a filter.

Optionally, the wire defines the periphery of the filter.

Optionally, the net extends from the first tube to the wire and the net runs along the first tube.

Optionally, the wire is of a resilient material and exhibits spring-like behavior.

Optionally, the wire extends along the first tube in a helical orientation between the first end of the wire and the second end of the wire.

Optionally, the wire extends through the second tube to outside the filter system.

Optionally, the wire attaches to the second tube.

Optionally, the filter system additionally comprises a third tube for moving over at least a portion of the first tube and at least a portion of the second tube, the third tube for enveloping the filter in the collapsed position, and for moving beyond the filter when the filter is in the expanded position.

Embodiments of the present invention are directed to a method for catching particulates associated with a medical procedure. The method comprises: providing a filtration system, deploying the filtration apparatus to the surgical site in the collapsed position; and causing the filter to expand outward to the expanded position into contact with tissue to form a barrier with the tissue, for catching and entrapping particulates. The filtration system comprises: a first tube; a second tube, the first tube and second tube movable relative to each other in at least a partially telescoping arrangement; and, a filter, a first end of the filter supported by the first tube and a second end of the filter supported by the second tube, the filter movable between a collapsed position when at least partially covered by the second tube, and an expanded position, when uncovered by the second tube.

Optionally, the tissue includes the walls of vessels.

Some embodiments of the present invention are directed to a method for catching particulates associated with a medical procedure. The method comprises providing a filtration apparatus comprising an outwardly expandable filter, a first end of the filter attached to an end of a first tube and a second end of the filter attached to an end of a second tube. The first and second tubes are arranged telescopically with respect to each other, with the first tube inside of the second tube, such that telescopic movement of the first and second tubes with respect to each other causes the filter to move from a folded-over, outwardly expanded, orientation to an inverted orientation. The filtration apparatus is then deployed to the surgical site such that the filter expands outward into contact with the walls of a vessel to form a barrier, for catching and entrapping embolic material particulates.

Optionally, the method additionally comprises moving the first tube and the second tube telescopically with respect to each other, such that substantially all of the filter is in an inverted orientation, for trapping and preventing backflow of particulates, inside the second tube.

Optionally, the method additionally comprises removing the filtration apparatus from surgical site, and also optionally, removing the filtration apparatus from the surgical site includes removing the filtration apparatus from the body.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIG. 1A is a perspective view of a system including some embodiments of the invention;

FIGS. 1B and 1C are perspective views of an area AA of FIG. 1A;

FIG. 1D is a perspective partial cut away view of the system of FIG. 1A showing attachments of a filter, in accordance with some embodiments of the invention;

FIG. 1E is a perspective cut away view of the area BB of FIG. 1D;

FIG. 1F is a perspective cut away view of the area CC of FIG. 1D;

FIG. 3A is a diagram of the position of all the catheters in their beginning state where all tubes are covering the filter;

FIG. 3B is a diagram after retraction of the over tube to release and allow expansion of a part of the filter to expand to a 2-layered funnel shaped member;

FIG. 3C is a diagram of the position of the catheters at the end of the procedure with the filter retracted and the inner and mid tubes covered by the over tube;

DETAILED DESCRIPTION OF THE DRAWINGS

Figure 2A:
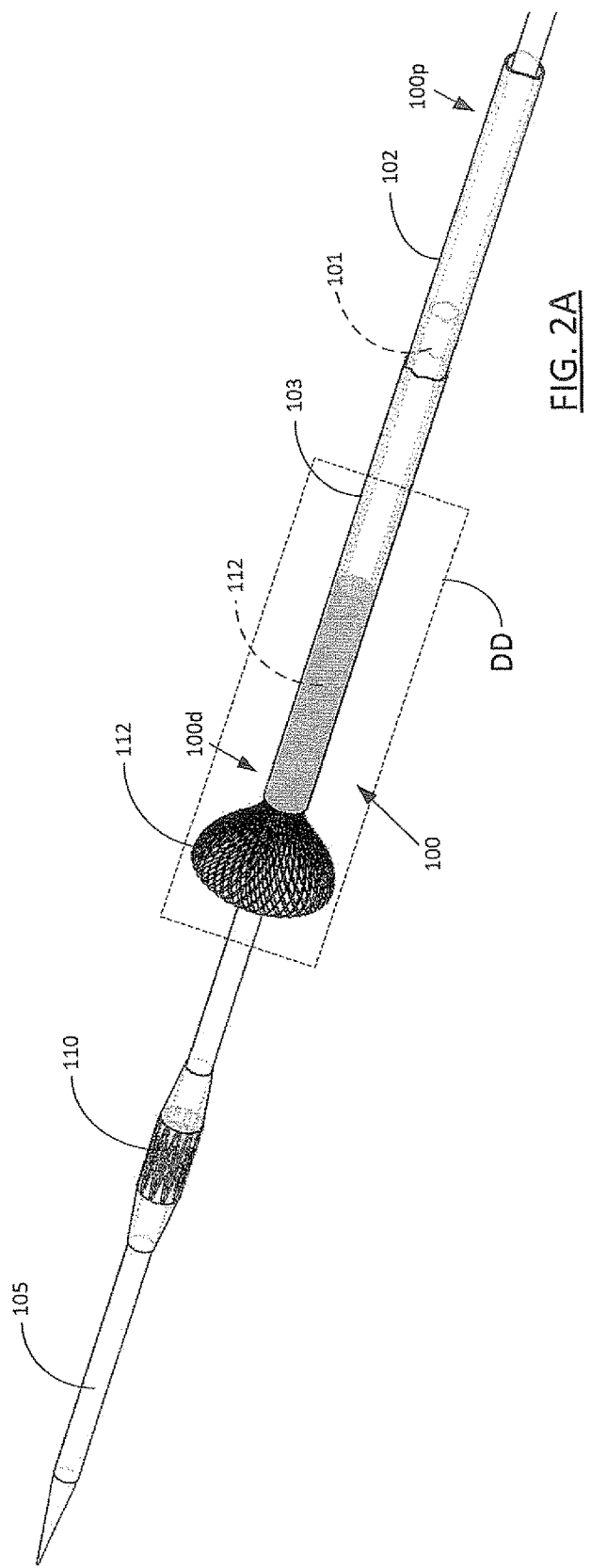
FIG. 2A is a perspective view of a the system of FIG. 1A showing the filter in an extended position.

FIGS. 1A-1F shows an apparatus 100, for example, a surgical tube system, in accordance with some embodiments of the invention. The apparatus 100 is formed of, for example, moving from inner to outer, an inner tube 101, a mid tube 102, and an over tube 103. The tubes 101-103 are typically in a telescopic arrangement with respect to each other, and are, for example, concentric and coaxial along a longitudinally extending axis.

The apparatus 100 is shown with a delivery catheter 105, which extends through the inner tube 101, and is shown supporting instrumentation, such as a stent supported valve 110 (hereinafter, "valve 110"). This stent supported valve 110 is formed of a stent 110a and valve 110b, as shown in detail in FIG. 3E, for implantation in the heart. Alternately, the valve 110 may be only a valve, absent support by a stent.

Throughout this document, a "tube" is any kind of surgical tube, catheter, instrument, device, or cannula having a cylindrical outer body with a hollow interior to accommodate additional tubes, catheters, instruments, devices, cannulas and the like.

While this three tube structure for the apparatus 100 is shown, additional tubes, strips or wires internal, intermediate and external may also be used with this apparatus 100. All of the tubes 101, 102, 103, are moveable with respect to each other, and steerable, individually and in combinations, by the operator. The same holds true for delivery catheter 105. The tubes 101-103 of the apparatus 100 system are, for example, conventional catheters, such as those commonly used in cardiac catheterization. The distal end of the apparatus 100 is represented by 100d, while the proximal end of the apparatus is represented by 100p. The distal end 100d, is typically within the body, while the proximal end 100p is typically outside the body, being manipulated by the operator performing the requisite procedure with the apparatus 100. All of the tubes 101-103 include distal and proximal ends oriented in accordance with the distal end 100d and the proximal end 100p of the apparatus 100. Movement in the distal direction, or distal movement, is in the direction of the distal end 100d, while movement in the proximal direction or proximal movement is in the direction of the proximal end 100p.

The inner 101 and mid 102 tubes support a filter 112. The filter 112 attaches to the inner tube 101 and the mid tube 202, as shown in FIGS. 1D, 1E 1F and 2B. As shown in detail in FIG. 2B which is a longitudinal section of this segment, the inner layer 112a of the filter 112 attaches, for example, to the distal end 101d of the inner tube 101 (e.g., at the inner tube 101 distal edge 101de) (FIG. 2B), or alternately, the inner side 101x of the inner tube 101 and, the outer layer 112b of the filter 112 attaches to the distal end 102d of the mid tube 102 (e.g., at the mid tube 102 distal edge 102de), or alternately, the outer side 102y of the mid tube 102 (FIG. 2B). The over tube 103 can, for example, serve as an introducer catheter for the apparatus 100.

The attachments of the filter 112 layers (inner layer 112a and outer layer 112b) to the respective inner 101 and mid 102 tubes, is, for example, by fasteners such as solder, glue and the like. Alternately, the filter layers 112a, 112b may also continue along the tube (inner tube 101 and mid tube 102) as a reinforcement. This attachment or the continuation arrangement allows for the filter 112 to be pushed and pulled, so that it folds inward, while the inner surface of the filter is pulled proximally whereby the embolic material, particulates and the like, is entrapped between the inner surface of the filter 112 and the shaft of the delivery catheter 105 in the filter 112.

The filter 112 is initially in a compressed position, where a short portion of the filter 112 is folded inward, and one end of the filter 112 is attached to the distal edge 101de of the inner tube 101, while the other end of the filter 112 is attached to the distal edge 102de of the mid-tube 102. The filter 112 is packed and covered by the over tube 103. The filter 112, is for example, of a medical grade material, such as nitinol or other metal alloys, medical grade stainless steel or, natural silk or synthetic wires or threads, such as PEEK (Polyether Ether Ketone) wire or thread or any of the aforementioned materials as braided or knitted wire of approximately 40-50 microns in diameter, resulting in openings of approximately 100 microns. This filter 112 size allows for the filter 112 to catch, trap and retain particulate, e.g., calcified tissue, plaque and other fatty tissue, which may come loose during the valve implant procedure, while allowing bold to flow through the filter 112. The material for the filter 112 is also flexible and resilient, allowing the filter 112 to expand outward, for example, radially, into a bell or funnel shape, when the over tube 103, is retracted from covering the filter 112, as shown in FIGS. 2A, 2B, 3B and 3D.

Turning also to FIG. 3A, the filter 112 is initially packed in a compressed (and folded) position (Position 0), where a portion of the filter 112 extends over the inner tube 101, as it is packed and covered by the over tube 103.

The filter 112 is folded such that it is double layered, such that particulates that may pass through the first or inner layer 112a are caught and trapped by the second or outer layer 112b. The unfolded filter 112 has openings up to 100 microns to allow blood flow but to capture embolic material larger than 100 microns. When folded upon itself, the double layered filter can capture smaller embolic material particles.

Figure 3D:
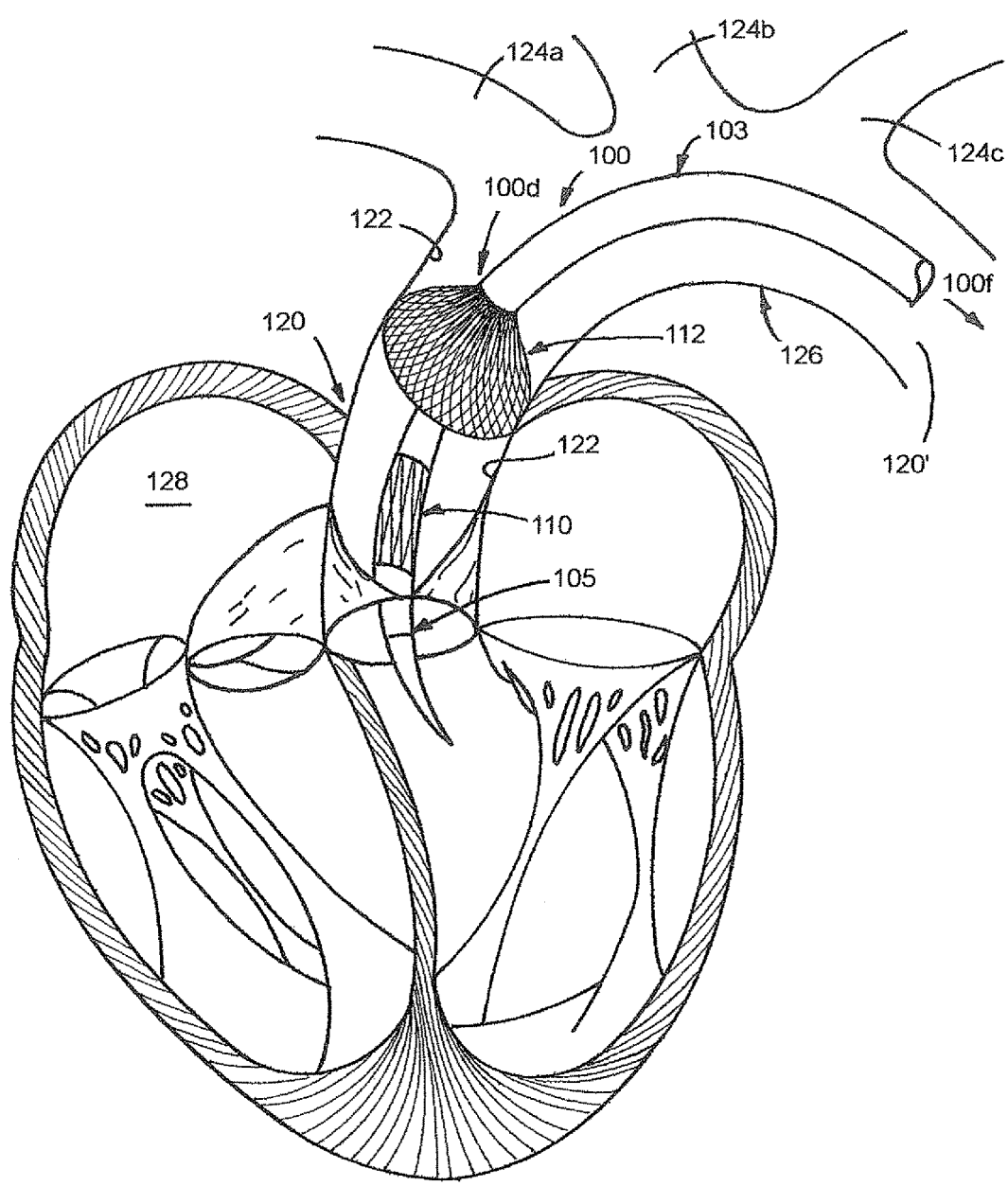
FIG. 3D is a diagram showing an exemplary operation of some embodiments of the invention of FIG. 1A.

An exemplary operation of the apparatus 100 is shown in FIG. 3D. Initially, the apparatus 100 has been deployed to the proper surgical site, for example, through the aorta 120, for a cardiac procedure such as Trans-Aortic Valve Replacement (TAVR), by conventional cardiac catheterization and access procedures, such as through vessels in the leg or the arm. Specifically, in FIG. 3D, the apparatus 100 is such that the filter 112 is proximally positioned with respect to the valve 110, and the apparatus 100 is inserted through the aorta, for example, by trans-aortic insertion.

Figure 3E:
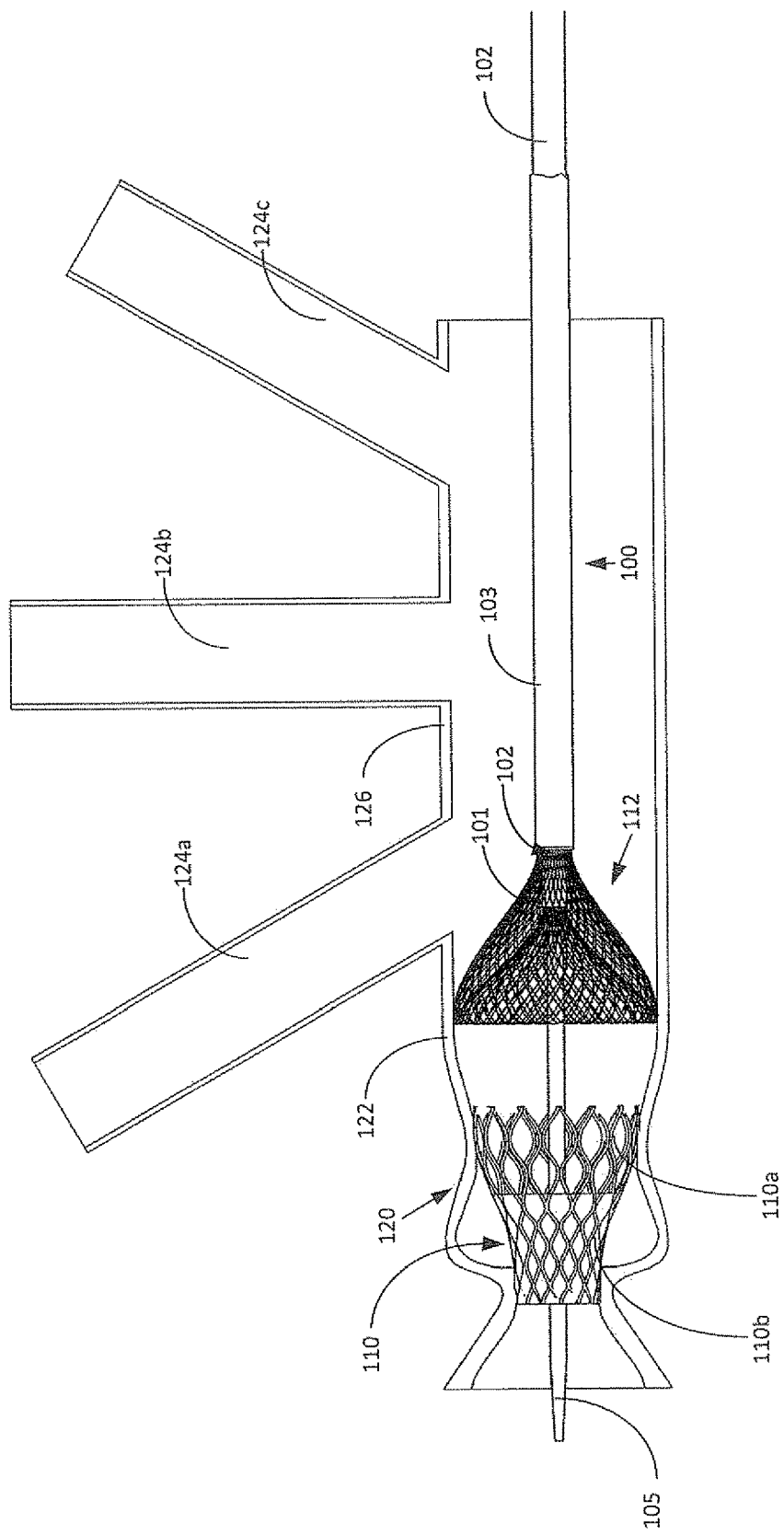
FIG. 3E is a sectional view of the apparatus of FIGS. 1A and 2A deploying a valve, which may be associated with a stent, in an exemplary operation.

The process of FIG. 3D continues as shown in FIG. 3E, where the apparatus 100 is such that the filter 112 is proximally positioned with respect to the stent supported valve 110. The apparatus 100 is inserted through the aorta 120, as a part of the delivery catheter 105, for example, by trans-aortic insertion. Insertion of the device can be done also through the subclavian or axillary artery.

To activate/expand the distal part of the filter 112, the over tube 103 is moved proximally, in the direction of the arrow 114, with respect to inner 101 and mid 102 tubes. The filter 112, upon release from the outermost over tube 103, expands outward, as per the arrow 115 (to Position 1 of FIG. 3B). The filter 112 expands, for example, into a bell/funnel shape, and its edges come into contact with the vessel walls, to block, capture and trap, particulate from traveling through the vessel to other unintended locations in the body, but allowing passage to blood to flow. The filter 112 expansion is such that the filter 112 extends to the vessel (i.e. aorta) 120 walls 122, and into contact with these walls 122, to form a barrier against particulate travel beyond the filter 112, as shown in FIG. 3D. Accordingly, particulates are caught and trapped between the filter 112 and the shaft of the delivery catheter 105, before the particulates can enter the blood vessels 124a-124c of the aorta 120 (brachio-cephalic arch 126), or flow downstream in the descending aorta 120' to other vessels or locations in the body. By catching and trapping the particulates in the filter 112, catastrophic outcomes, caused by particulates, such as vessel and organ blockages, strokes, and the like, can be prevented.

The delivery catheter 105 is movable within the inner tube 101 and the filter 112, to perform the requisite procedure, e.g., valve replacement, in the heart 128. When the valve deployment system reaches its target the overtube 103 is moved proximally to allow expansion of the filter. Then the mid tube 102 is pushed distally (in the direction of the arrow 116a), while the inner tube 101 is pulled proximally (in the direction of the arrow 116b), for example, simultaneously or contemporaneously, such that the inner layer 112a of the filter 112 retracts around the delivery catheter. The inner tube 101 is positioned proximally with respect to the distal end of the mid tube 102, as the filter 112 is now extending between the distal ends of the mid 102 and inner 102 tubes. At the end of the procedure the over tube 103 is moved distally (in the direction of the arrow 117), to cover the end of the filter 112 (Position 2 of FIG. 3C).

With the filter 112 now within the apparatus 100, the inner tube 101 and the mid tube 102, with the filter 112 (and the caught and trapped particulates), together with the valve delivery system can be removed from the body. This is performed, for example, by the inner 101 and mid 102 tubes being pulled proximally through the over tube 103, leaving the body through the vessels in the leg or arm.

Figure 2B:
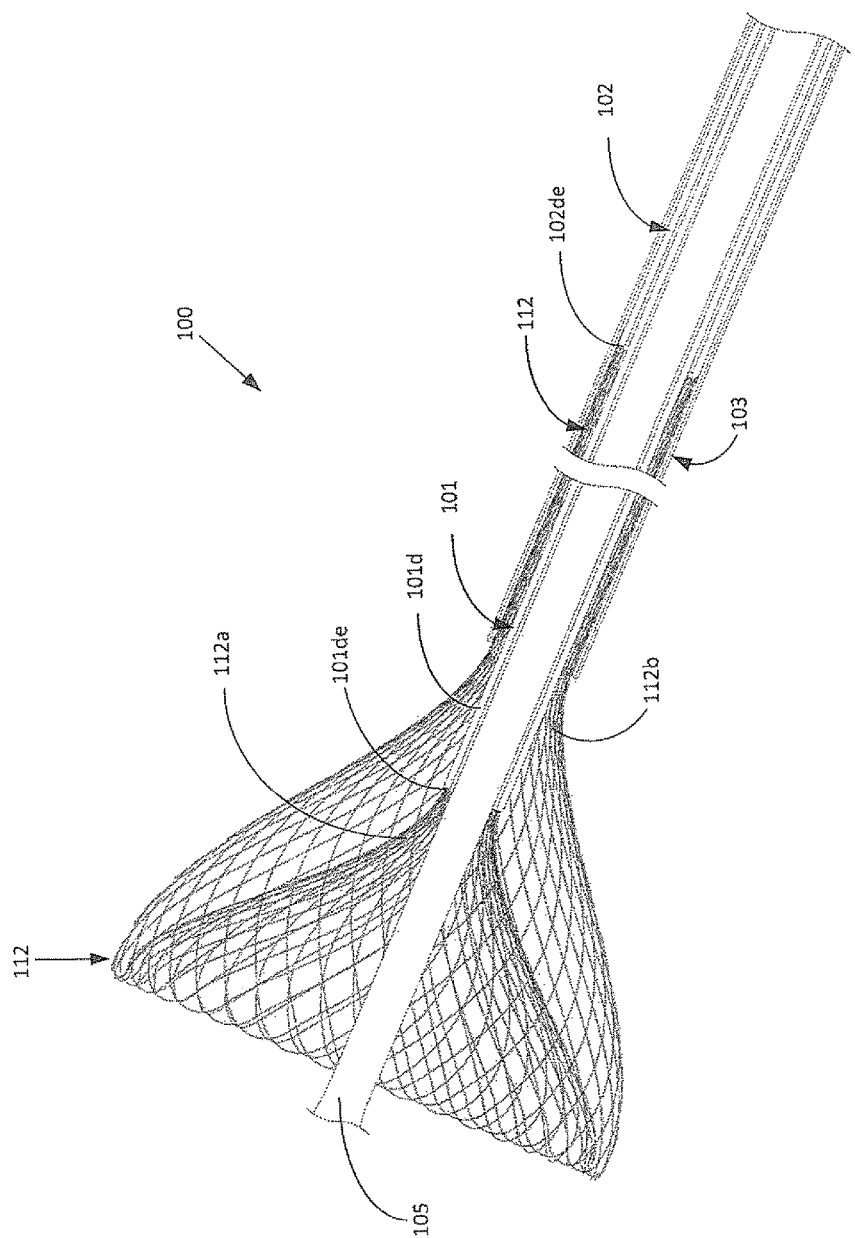
FIGS. 2B is a longitudinal section an area DD of FIG. 2A.

Alternatively, the filter 112 may attached to the inner 101 and mid 102 tubes as shown above, with the inner 101 and mid 102 tubes joined, resulting in a double layer static filter, which would look and function similar to the filter 112 of FIGS. 2A and 2B. In such a case there is no relative movement between the inner 101 and the mid tube 102, due to their being joined. As a result, this alternative filter would maintain the folded over bell shape, upon the filter being released from the over tube 103. The filter 112 subsequently returns to its retracted or packed state, when the over tube 103 is moved (distally) over the filter 112, or when the fixed mid 102 and inner 101 tubes are moved proximally, or combinations of these movements, when removal of the inner 101 and mid 102 tubes with the filter 112, from the body is desired.

While the apparatus 100 is shown in a cardiac operation, this is exemplary only. The catheter system 100 can be used in other body locations and vessels, including other blood vessels, bile ducts and other ducts, urinary tracts, and brain passageways and other tubular structures in the body. Additionally, while a double layer filter is shown, other multiple layer bell shaped filters are also permissible.

Figure 4:
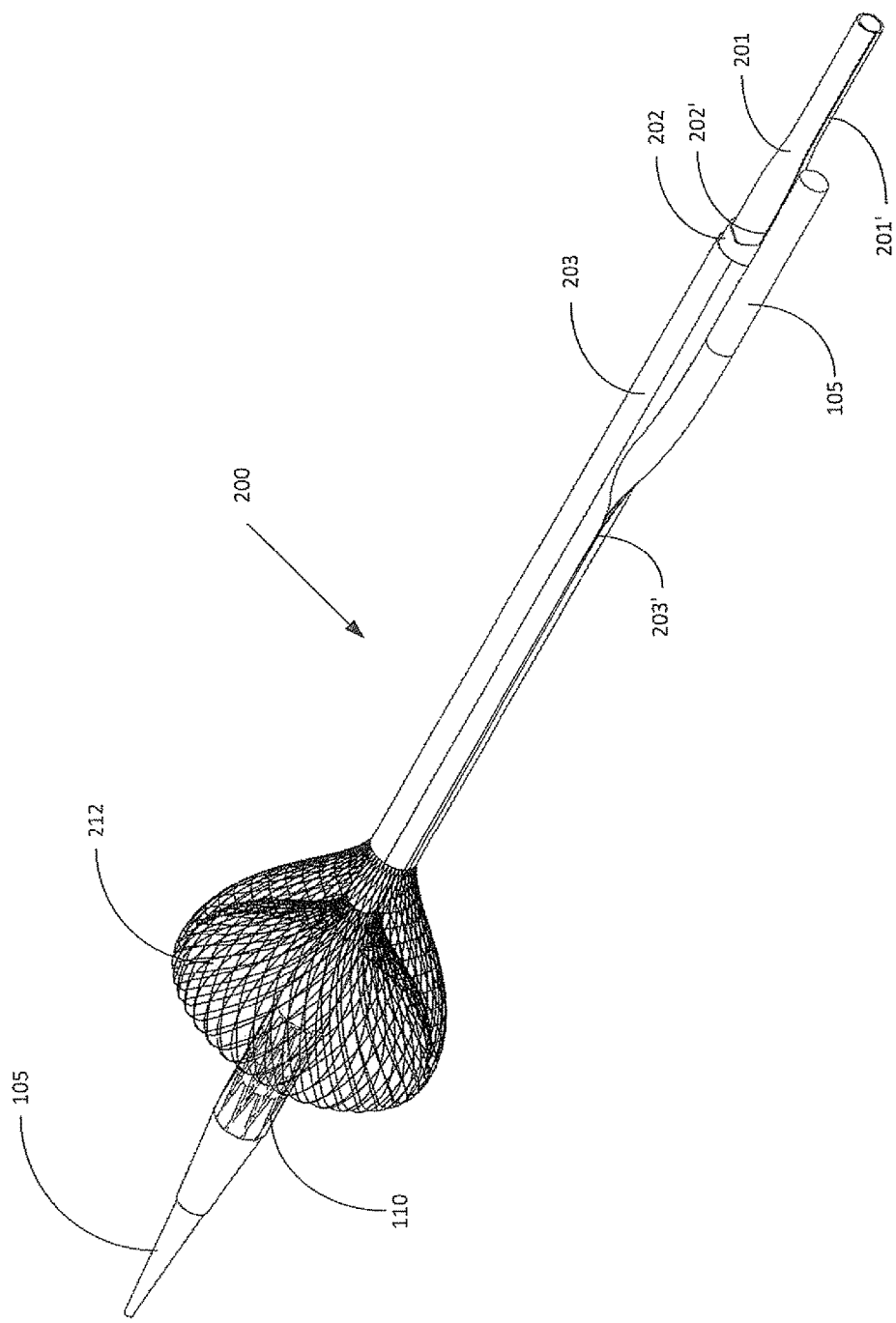
FIG. 4 is a perspective view of an alternative apparatus in accordance with embodiments of the present invention.

FIG. 4 shows an alternative apparatus 200, with a filter 212. This apparatus 200 is similar in all aspects and operation to the apparatus 100, with similar components having the same numbering as in the apparatus 100, but in the 200's, whose components which are not specifically mentioned in accordance with those for the apparatus 100. In this alternative apparatus 200, the over tube 203 (and also the inner 201 and mid 202 tubes) are split to accommodate the delivery catheter 105 in their respective central lumens. The splits 203', 202', 201' typically extend longitudinally and is movable laterally outward, to accommodate the passage of the delivery catheter 105 (with the valve 110), when the delivery catheter 105 is moved distally, through the three tubes 201, 202, 203.

This split over tube 203 (and split inner 101 and mid 102 tubes) allows for the additional size, e.g., diameter of the delivery tube 105, for example, with the valve 110, to pass through these tubes 201, 202, 203 to a position for deployment, such as that shown in FIG. 3D. With the passage of the valve end complete, the over tube 203, mid tube 202 and inner tube 201 all move inward to their original positions. The over tube 203, mid tube 202 and inner tube 201 are movable between its inward and outward orientations due to their being made of a resilient material, metal or nitinol wire reinforced.

Figure 5A:
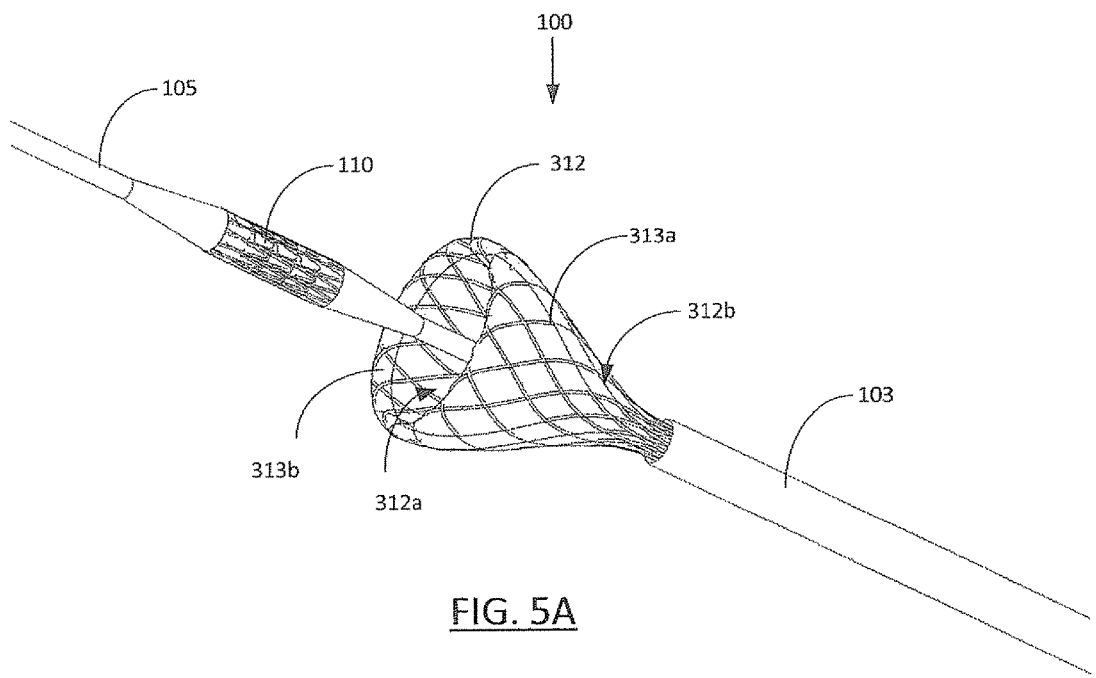
FIG. 5A is a perspective view of another alternative apparatus in accordance with embodiments of the present invention.

FIG. 5A shows an alternative filter 312 for the apparatus 100. The filter 312 formed of a support structure 313a or frame of braided nitinol or metal mesh 313a, and dense net or mesh 313b, over the support structure 313a. The net or mesh 313b performs embolic material filtering. The filter 312 includes inner 312a and outer 312b layers that attach to the respective inner 101 and mid 102 tubes of the apparatus similar to that for the filter 112, as detailed above. The filter 312 is such that the covering net or mesh 313b is of materials such as nitinol, polymer fibers or silk, at porosities such as 80-150 microns.

Figure 5B:
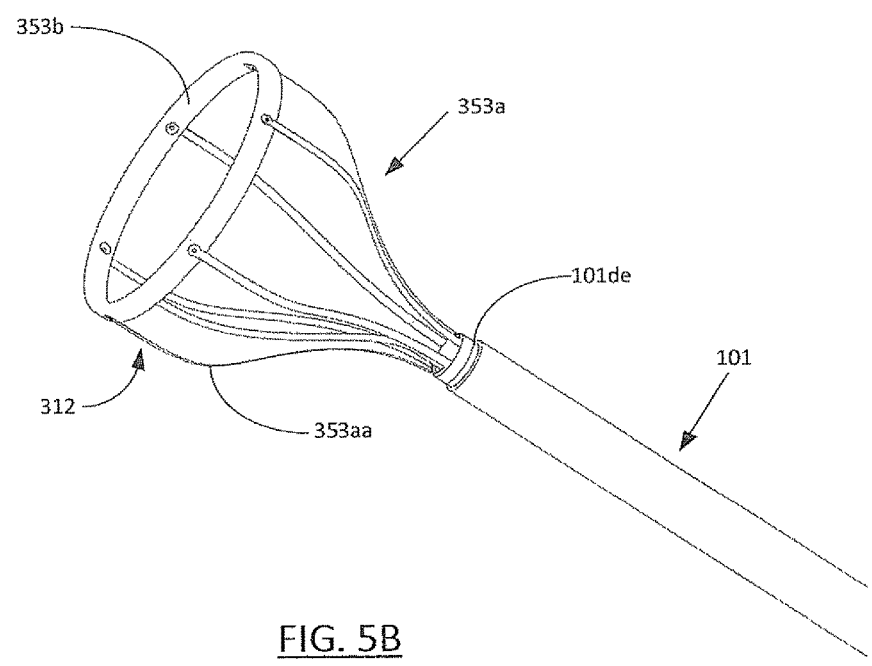
FIG. 5B is a perspective view of an alternative filter support mechanism of the embodiment of FIG. 5A; and, FIGS. 6A, 6B and 6C are perspective views of an alternative apparatus in accordance with embodiments of the present invention.

FIG. 5B shows an alternate filter 312' to that of the filter 312 of FIG. 5A, for use with the apparatus 100, as detailed above. The filter 312' is retractable, e.g., collapsible, and extendable, e.g., expandable, from a tube of the apparatus 100, for example, the inner tube 101. Alternately, the filter 312' may be mounted on an inner tube 101 or mid tube 102, for example, at the distal edges 101de, 102de of the inner tube 101 or mid tube 102, respectively, similar to that for the filter 112 detailed above. The filter 312' is retracted from the respective inner 101 or mid 102, similar to that described for the filter 112 above.

The filter 312' is formed of frame 353a of metal wires 353aa, for example, in a bell shape, which in turn, connect to a balloon 353b, or other outwardly expanding support member. The balloon 353b is typically in a peripheral ring at the distal end of the frame 353a that is inflatable, with air, gas, liquid or the like, to support the distal end of the frame 353a in the expanded position as shown for supporting the inward rolling filter net or mesh. The balloon is inflated through one of the arms of the frame which is tubular The frame 353a, in particular, the wires 353aa, serve to support a net or mesh (not shown), which is similar to the net or mesh 313b, 413b, 413c detailed above for filters 312, 412, respectively.

Figure 6A:
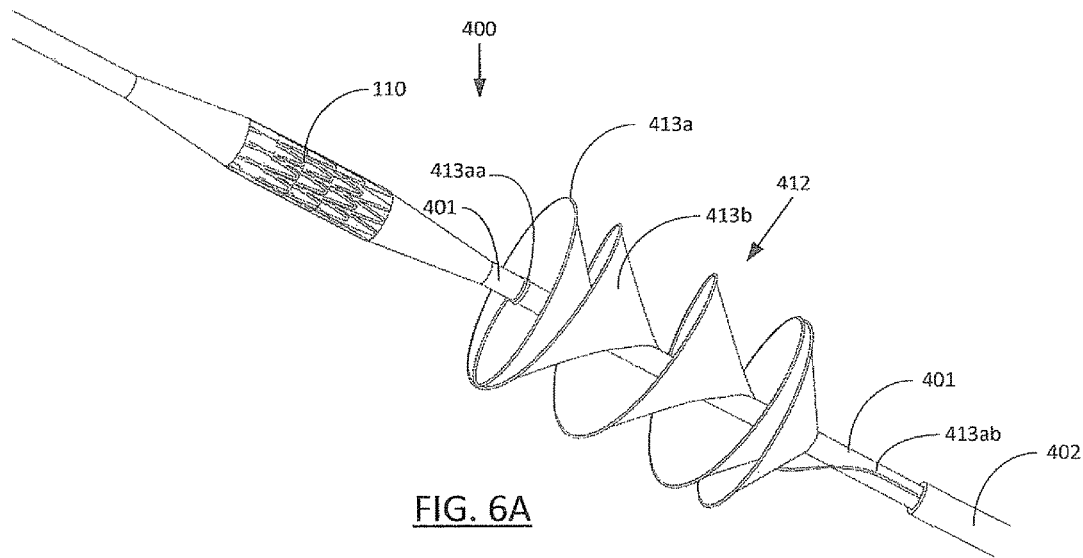
Figure 6B:
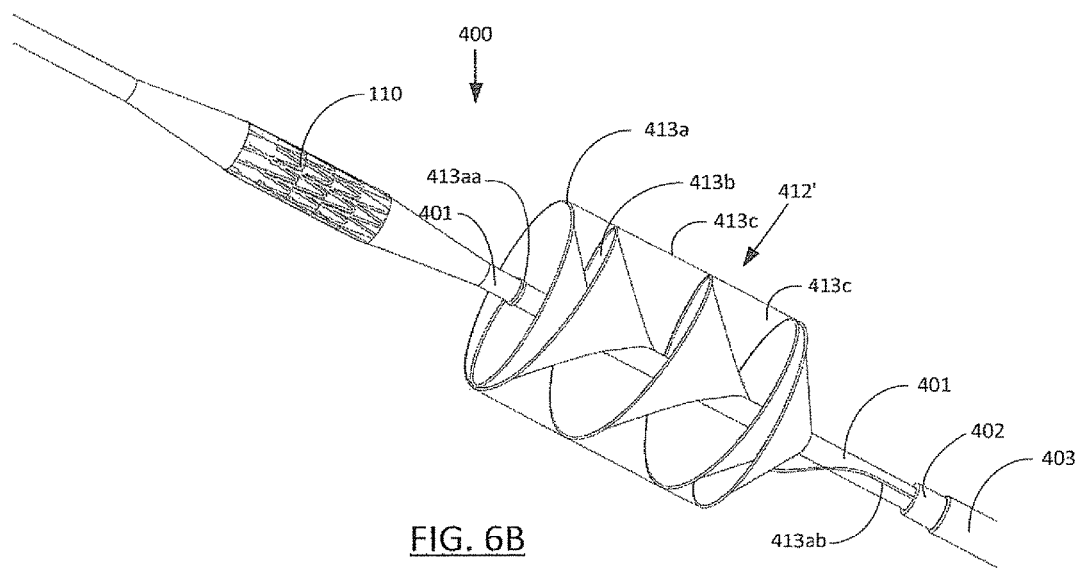
Figure 6C:
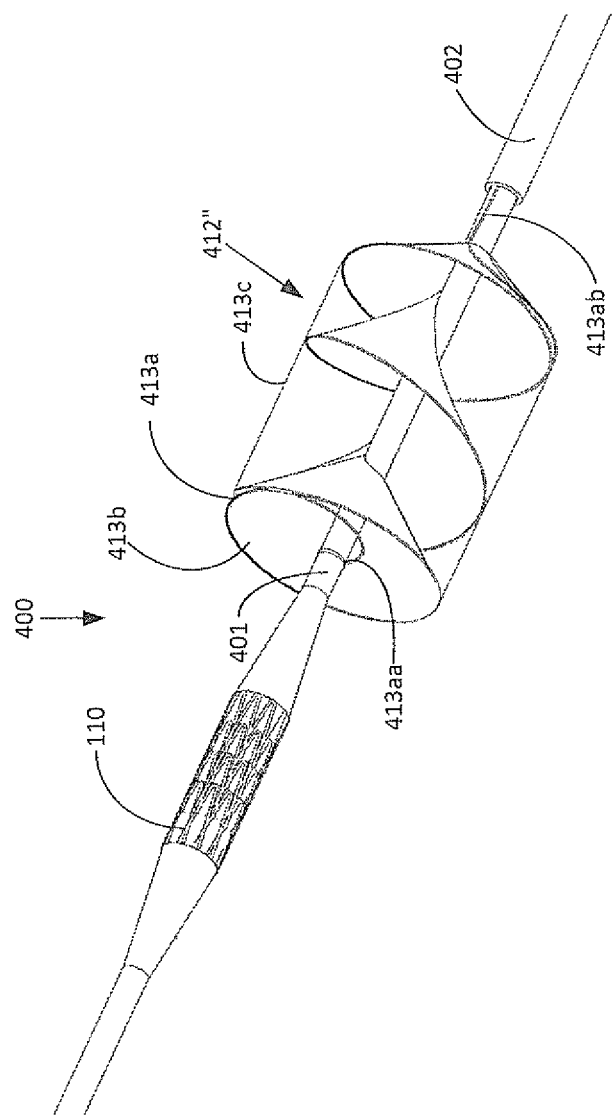

FIGS. 6A-6C show an alternative apparatus 400 formed of an inner tube 401 and a mid tube 402, with an overtube 403, in a telescoping arrangement, and for example, concentric and coaxial along a longitudinal axis. The inner tube can be the valve delivery catheter. These alternative apparatus 400 include filters 412, 412', 412". These filters 412 of FIG. 6A, 412' of FIG. 6B, and 412" of FIG. 6C are spiraling filters. For example, the spirals result in conical filter segments, with the cones pouting proximally. The spirals are arranged serially, to catch particles that could pass through previous upstream spirals. Elements of the apparatus 400 which are not specifically mentioned, but have the same numbers in the "400s" as the apparatus 100, the structures of the alternative apparatus 400 are similar to those detailed above for the apparatus 100, and are in accordance with the descriptions provided above.

Each spiraling filter 412, 412', 412" includes a pre-shaped support, such as a wire 413a, oriented, for example, in a helix, defining the periphery of the filter 412, 412', 412". The wire 413a, is for example, nitinol, or any other suitable material, with nitinol typically used due to its shape memory retaining properties, as well as its spring-like behavior (e.g., resilience). The wire 413a defines the outer periphery of the filter 412, 412', 412", and supports a ribbon-shaped net 413b. The net 413b is similar to the net or mesh detailed above, for fine filtration. The inner edge 413bx connects to the shaft of the inner tube 401. The inner tube 401 may also serve, for example, as a delivery catheter for the instrumentation, such as the valve 110, similar to that as described above for the delivery catheter 105.

The inner edge 413bx of the net 413b attaches to the inner tube 401 in a spiral manner, for example, either by a mechanical attachment, including by being wrapped around the inner tube 401. The distal end 413aa of the wire 413a attaches to the inner tube 401 at the distal end of the inner tube 401. The proximal end 413ab of the wire 413a attaches to the mid-tube 402, or extends through the inner tube 401 or mid tube 402, to outside of the apparatus 400, where it can be manipulated, for example, pulled to collapse the filter 412, 412', 412", by the operator.

The filters 412, 412', 412" are expandable from the mid tube 402, when the mid tube 402 or over tube 403 are moved proximally, inner tube 401, and in some instances, the mid tube 402) are moved distally, allowing the filter 412, 412', 412" to release, such that it expands laterally outward. The filters 412, 412', 412" are retractable into the mid tube 402 and/or the over tube 403 (when the wire 413a is pulled by the mid tube 402). Both of these aforementioned actions cause the filter 412, 412', 412" to collapse. The mid tube 402 and the inner tube 401 are then moved proximally into the over tube 403, or the mid tube 402/over tube 403 is moved distally over the now-collapsed filter 412, 412', 412" of the inner tube 401.

Should the proximal wire 413ab extend through the inner tube, pulling the proximal end of the wire will collapse the filter. The apparatus 400 of FIGS. 6B and 6C include a net or mesh sleeve 413c around the respective filters 412', 412", of a net or mesh material the same or similar to that of the net or mesh 413b detailed above. This net or mesh sleeve 413c serves as an additional protective filtration element for particles that can escape from the outer sides of the filter 412', 412", as defined by the wire 413. FIG. 6B differs from FIG. 6C, as it may protect the openings of the arteries 124a-124c of the brachiocephalic arch 126 (FIG. 3D, 3E) reaching the brain in case particles escape between the edges of the filter or if the entire apparatus 400 is positioned in a manner that it cannot protect these arteries. FIG. 6B also differs from FIG. 6C as the respective filters 412', 412" can be collapsed, as wire 413ab is pulled by proximally pulling the mid tube 402, whereas in FIG. 6C the wire 413ab is pulled directly.

The present invention, while shown for human use, is also suitable for animal use.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A filter system comprising:
    a first tube;
    a second tube, the first tube and second tube moveable relative to each other in at least a partially telescoping arrangement;
    a filter, a first end of the filter supported by the first tube and a second end of the filter supported by the second tube, the filter moveable between a collapsed position when at least partially covered by the second tube, and an expanded position, when uncovered by the second tube; and,
    a delivery catheter for passage of instrumentation through the first tube to a predetermined site.

2. The filter system of claim 1, wherein the filter includes a frame and a mesh covering the frame.

3. The filter system of claim 2, wherein the filter comprises a foldable member moveable by the movement of the first and second tubes from a folded-over outwardly expanded orientation, defining the expanded position, to an inverted orientation defining the collapsed position.

4. The filter system of claim 3, additionally comprising: a third over tube for enveloping the first and second tubes, the first tube defining an inner tube and the second tube defining a mid tube, the third tube moveable so as to cover and uncover the filter, the first, second and third tubes moveable with respect to each other.

5. The filter system of claim 4, wherein the first, second and third tubes are telescopically arranged with respect to each other.

6. The filter system of claim 5, wherein each of the first, second, and third tubes include a longitudinally extending slit for allowing the first, second and third tube to temporarily separate laterally outward along the longitudinally extending slit to accommodate instrumentation passing through the first, second and third tubes.

7. The filter system of claim 6, wherein the first second and third tubes are made of a resilient material to accommodate laterally outward movement of the tube portions on oppositely disposed sides of the longitudinally extending slit from an open closed position to an open position and the for returning the first, second, and third tubes to the closed position once the instrumentation has passed through the first, second, and third, tubes.

8. The filter system of claim 1, wherein the instrumentation includes at least one of stents and valves.

9. The filter system of claim 1, wherein the filter comprises:
    a wire including a first end in communication with the first tube, and, a second end extending into the second tube; and,
    a net supported by the wire, to define a filter.

10. The filster system of claim 9, wherein the wire defines the periphery of the filter.

11. The filter system of claim 10, wherein the net extends from the first tube to the wire and the net runs along the first tube.

12. The filter system of claim 11, wherein the wire is of a resilient material and exhibits spring-like behavior.

13. The filter system of claim 12, wherein the wire extends along the first tube in a helical orientation between the first end of the wire and the second end of the wire.

14. The filter system of claim 11, wherein the wire extends through the second, tube to outside the filter system.

15. The filter system of claim 11, wherein the wire attaches to the second tube.

16. A filter system comprising:
    an outwardly expandable filter, a first end of the filter attached to an end of a first tube and a second end of the filter attached to an end of a second tube, the first and second tubes arranged telescopically with respect to each other such that telescopic movement of the first and second tubes with respect to each other causes the filter to move from a folded-over outwardly expanded orientation to an inverted orientation; and,
    a delivery catheter for passage of instrumentation through the first tube to a predetermined site.

17. The filter system of claim 16, wherein the filter includes a frame and a mesh covering the frame.

18. The filter system of claim 16, wherein the instrumentation includes at least one of stends and valves.

19. The filter system of claim 16, additional comprising: a third over tube for enveloping the first and second tubes, the first tube defining an inner tube and the second tube defining a mid tube, the third tube moveable so as to cover and uncover the filter, the first, second and third tubes movable with respect to each other.

20. The filter system of clam 19, wherein the first, second and third tubes are telescopically arranged with respect to each other.

21. The filter system of claim 20, wherein each of the first, second, and third tubes include a longitudinally extending slit for allowing the first, second and third tube to temporarily separate laterally outward along the longitudinally extending slit to accommodate instrumentation passing through the first, second and third tubes.

22. The filter system of claim 21, wherein the first second and third tubes are made of a resilient material to accommodate laterally outward movement of the tube portions on oppositely disposed sides of the longitudinally extending slit from an open closed position to an open position and the for returning the first, second, and third tubes to the closed position once the instrumentation has passed through the first, second, and third, tubes.

* * * * *